United States Patent
Prein et al.

(10) Patent No.: US 7,301,056 B2
(45) Date of Patent: Nov. 27, 2007

(54) PROCESS FOR THE SEPARATION OF PHENOL FROM PHENOL-CONTAINING STREAMS FROM THE PREPARATION OF BISPHENOL A

(75) Inventors: Michael Prein, Krefeld (DE); Rob Eek, Leverkusen (DE); Raymond Audenaert, Hamme (BE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/168,025

(22) Filed: Jun. 28, 2005

(65) Prior Publication Data
US 2006/0004234 A1 Jan. 5, 2006

(30) Foreign Application Priority Data
Jul. 2, 2004 (DE) .................. 10 2004 032 232

(51) Int. Cl.
*C07C 37/68* (2006.01)
(52) U.S. Cl. ..................................... 568/749
(58) Field of Classification Search ................. 568/749
See application file for complete search history.

(56) References Cited

U.S. PATENT DOCUMENTS 5,785,823 A 7/1998 Meurere et al. ............. 203/71
6,133,486 A * 10/2000 Maas et al. ................. 568/749

FOREIGN PATENT DOCUMENTS

EP 812 815 A2 12/1997
JP 57059926 * 4/1982

OTHER PUBLICATIONS

Willems et al, "Kinetic Modeling of the Thermal-Cracking of Hydrocarbons. 2. Calculation of Activation Energies", American Chemical Society, 1998, pp. 1966-1971.*
Willems et al ("Kinetic Modeling of the Thermal Cracking of Hydrocarbons. 2. Calculation of Activation Energies", American Chemical Society, 1998, pp. 1966-1971).*

* cited by examiner

*Primary Examiner*—Yvonne Eyler
*Assistant Examiner*—Kellette Gale
(74) *Attorney, Agent, or Firm*—Aron Preis

(57) ABSTRACT

A continuous process for the separation of phenol is disclosed. The process includes (a) feeding a stream of material, produced while preparing bisphenol A by reacting phenol with acetone, into a distillation column containing at least 5 theoretical separation stages, b) distilling-off the phenol as a top product and discharging from the column a bottom product containing secondary components, c) continuously introducing a portion of the bottom product into a dwell-time container operating at process parameters sufficient to cause, in the presence of an acidic catalyst, at least partial isomerization of the secondary components to form an isomerized product and d) introducing the isomerized product to the distillation column. The introducing of the bottom product is at a rate that is more than 30% of the rate of feeding of the stream at temperatures greater than 190° C. and hydrodynamic dwell time of at least 120 minutes.

4 Claims, 1 Drawing Sheet

PROCESS FOR THE SEPARATION OF PHENOL FROM PHENOL-CONTAINING STREAMS FROM THE PREPARATION OF BISPHENOL A

FIELD OF THE INVENTION

The invention concerns phenol and in particular to its separation from streams resulting in the production of Bisphenol-A.

TECHNICAL BACKGROUND OF THE INVENTION

Bisphenols as condensation products of phenols and carbonyl compounds are starting materials or intermediates for the production of a large number of commercial products. The condensation product from the reaction of phenol and acetone, 2,2-bis(4-hydroxyphenyl)propane (bisphenol A, BPA), is of particular industrial importance. BPA is used as the starting material for the production of various polymeric materials, such as, for example, polyarylates, polyether imides, polysulfones and modified phenol-formaldehyde resins. Preferred fields of application are the production of epoxy resins and polycarbonates.

The industrially relevant preparation methods for BPA are based on the acid-catalyzed reaction of phenol with acetone, a phenol-acetone ratio of >5:1 preferably being established in the reaction. As acidic catalysts there may be used both homogeneous and heterogeneous Bronstedt or Lewis acids, for example strong mineral acids such as hydrochloric or sulfuric acid. Gel-like or macroporous sulfonated crosslinked polystyrene resins (acidic ion exchangers) are preferably used. The embodiments hereinbelow relate to a process using acidic ion exchangers as catalysts. These may be mono- or hetero-disperse.

In order to achieve high selectivities, the reaction of phenol with acetone is carried out in the presence of suitable mercapto compounds as co-catalysts. These may either be homogeneously dissolved in the reaction solution or fixed to the sulfonated polystyrene matrix via ionic or covalent bonds. The reaction unit is a stratified bed or fluidized bed, through which the solution flows upwards or downwards, or a column such as a reactive distillation column.

The selectivity of the reaction, as well as the long-term storage stability of the catalyst, are determined by the quality of the raw materials phenol and acetone that are used. For the preparation in particular of BPA as a raw material for high-quality plastics such as, for example, polycarbonate, very high demands are therefore made of the purity of the basic materials phenol and acetone that are used. Typically, purities of >99.95 wt. % for phenol and >99.90 wt. % for acetone, with at the same time low contents of impurities (S<0.5 ppm, Fe<1 ppm), are regarded as being positive for the achievement of high product purities and for minimizing catalyst deactivation. For example, EP-A-876 319 describes freeing commercial phenol of troublesome impurities by treatment with molecular sieve and thus ensuring better usability in a process for BPA preparation.

EP-A-680 913 describes the use of modified acidic ion exchangers to remove hydroxyacetone from phenol for BPA synthesis.

The reaction of phenol with acetone in the presence of acidic catalysts and mercapto compounds as co-catalysts yields a product mixture that contains unreacted phenol and optionally acetone and primarily BPA and water. In addition, small amounts of typical side products of the condensation reaction are formed, for example 2-(4-hydroxyphenyl)-2-(2-hydroxyphenyl)propane (o,p-BPA), substituted indanes, hydroxyphenylindanols, hydroxyphenyl-chromanes, substituted xanthenes and more highly condensed compounds having three or more phenyl rings in the molecular framework.

The mentioned side products, as well as water, phenol and acetone, impair the suitability of BPA for the production of polymers and must be separated off by suitable processes. For the production of polycarbonate in particular, high demands are made of the purity of the raw material BPA.

The working up and purification of BPA is carried out by a multi-stage cascade of Suitable purification processes such as, for example, suspension crystallization, melt crystallization, distillation and/or desorption. In an industrially preferred form, BPA is separated from the reaction mixture in the form of an approximately equimolar crystalline adduct with phenol by cooling the reaction mixture with crystallization of the BPA/phenol adduct. The crystallization is preferably carried out in the form of suspension crystallization. The BPA/phenol adduct crystals are subsequently separated from the liquid phase by means of a suitable apparatus for solid/liquid separation, such as rotary filters or centrifuges, and fed to further purification. Adduct crystals so obtained typically have a purity of >99 wt. % BPA, based on BPA and the side products with a phenol content of about 40 wt. %, based on the total amount of adduct crystals. By washing with suitable solutions, which typically contain one or more components from the group acetone, water, phenol, BPA and side products, the adduct crystals may be freed of impurities adhering to the surface. The BPA/phenol adduct crystals obtained following the above-described suspension crystallization of the reaction solution and solid/liquid separation are fed to more extensive purification steps, wherein phenol is separated off and, optionally, a reduction in the concentration of side products is achieved by the use of suitable purification operations (suspension crystallization, layer crystallization, extraction, distillation).

The stream of liquid obtained in the solid/liquid separation (mother liquor) contains phenol, BPA, water formed in the reaction, unreacted acetone, and is rich in the side products typically formed in the preparation of BPA. In a preferred form, this stream of mother liquor is fed back into the reaction unit. In order to maintain the catalytic activity of the acidic ion exchanger, all or some of the water that has formed is removed beforehand by distillation, any acetone that is still present is also removed wholly or partially from the mother liquor. The dewatered reaction stream so obtained is supplemented with phenol and acetone and fed back into the reaction unit. Alternatively, it is possible to remove water and acetone wholly or partially by distillation before the suspension crystallization of the BPA/phenol adduct is carried out. In the mentioned distillation steps, a portion of the phenol present in the reaction solution may also be separated off by distillation.

Such a closed-circuit procedure has the disadvantage that side products of the BPA preparation become concentrated in the circulating stream; these side products adversely affect the purity of BPA in the suspension crystallization and may lead to deactivation of the catalyst system. In order to avoid excessive concentration of side products in the circulating stream, a portion of the mother liquor mixture must be discharged from the system. The amount of side products removed from the process in this manner must correspond in the equilibrium state to the amount of side products formed in the reaction. The discharge is typically effected by removing a portion of the mother liquor from the circulating stream, it being possible for water of reaction that has formed, unreacted acetone and portions of phenol optionally to be removed by distillation beforehand. The composition of the mother liquor at this point, and accordingly also the composition of the discharged portion, typically consists of from 70 to 90 wt. % phenol, from 3 to 15 wt. % BPA and from 3 to 15 wt. % side products and isomers formed in the reaction. Because ultimately only the last-mentioned portion of side products has to be removed from the process, the discharged amount is subjected to further working-up steps in order to minimize losses of material.

In a simple form, phenol is distilled off to a residual content of <10 wt. %, so that a residual resin having a content of <10 wt. % phenol, from 15 to 85 wt. % BPA and from 15 to 85 wt. % side products is obtained, which resin is removed from the process and disposed of, for example, by burning or dumping.

In another form, a portion of the BPA contained in the discharged amount is recovered by distilling off a portion of the phenol from the discharged portion and feeding the concentrated solution so obtained to suspension crystallization and subsequent solid/liquid separation. It has proved advantageous here to pass the discharged amount, before or after the partial separation of phenol, over a rearrangement unit filled with acidic ion exchanger. This unit is generally operated at higher temperatures than the reaction unit. In this rearrangement unit, under the conditions prevailing therein, some of the side products of the BPA preparation present in the circulating stream are isomerized to BPA, so that the total yield of BPA may be increased. In the solid/liquid separation, a portion of the BPA that is present is obtained in the form of a BPA/phenol adduct crystal and may be fed to further purification steps. A filtrate typically consisting of from 60 to 90 wt. % phenol, from 3 to 12 wt. % BPA and from 3 to 18 wt. % side products is additionally obtained. The phenol contained in this filtrate is distilled off to a residual content of typically <10 wt. % and the resulting residual resin, containing <10 wt. % phenol, from 14 to 80 wt. % BPA, from 20 to 86 wt. % side products, is fed to disposal.

The described processes for the working up of the discharged stream have the disadvantage that relatively large amounts of phenol, either in undissolved form or bonded in BPA or the side products, are still present in the residual resin that is finally disposed of Disposal of the residual resin accordingly leads to a loss of raw materials.

The object of the present invention was therefore to find a process for the working Lip of discharged streams from a BPA production process, with which process phenol is obtained in high purity and in high yields.

Such a process preferably meets the following demands:
1. minimization of phenol in the residual resin,
2. minimization of BPA in the residual resin,
3. minimization of the amount of residual resin,
4. provision of phenol of high purity (>99.8%) and having low contents of impurities (S, Fe, Cl) from the working-up process with high yields,
5. continuous procedure with minimal use of apparatus and energy.

SUMMARY OF THE INVENTION

Figure 1:
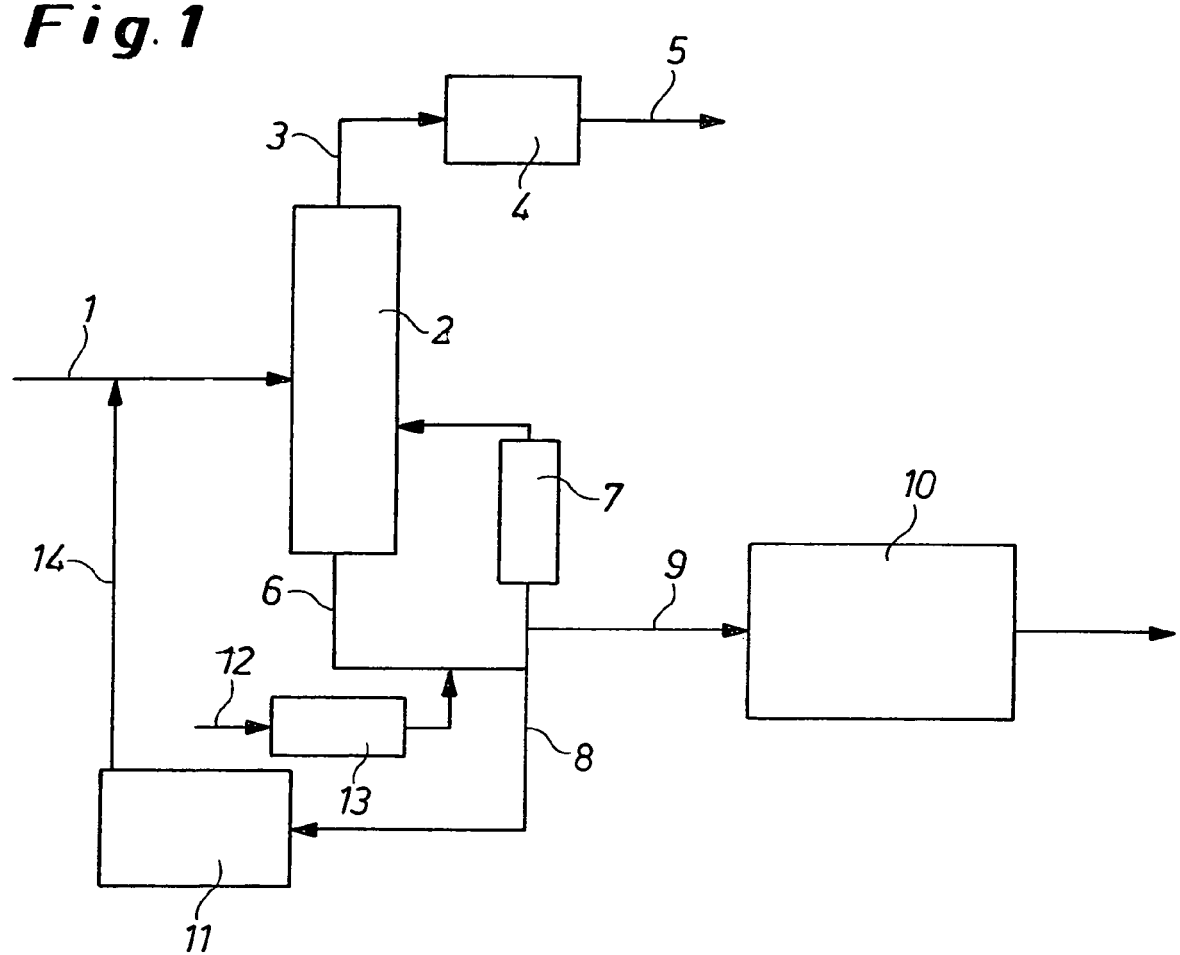
FIG. 1 is a schematic representation of the preferred process.

A continuous process for the separation of phenol is disclosed. The process includes a) feeding a stream of material containing 40 to 90% phenol, 5 to 40% bisphenol A and 5 to 40% of side products into a distillation column containing at least 5 theoretical separation stages, b) distilling-off the phenol as a top product and discharging from the column a first portion of the bottom product that contains side products, c) continuously introducing a second portion of the bottom product into a dwell-time container operating at process parameters sufficient to cause, in the presence of an acidic catalyst, an at least partial isomerization of the side products to form an isomerized product and d) introducing the isomerized product to the distillation column. The introducing of said portion of the bottom product is at a rate, in Kg/hour, that is more than 30% of the rate of feeding of the stream, and the dwell-time container is run at process parameters including temperatures greater than 190° C. and hydrodynamic dwell time of at least 120 minutes.

DETAILED DESCRIPTION OF THE INVENTION

The invention relates to a process for the continuous separation of phenol from a discharge stream, produced in the preparation of bisphenol A and containing from 40 to 90 wt. % phenol, from 5 to 40 wt. % bisphenol A and from 5 to 40 wt. % side products formed in the reaction of phenol and acetone to give bisphenol A, in which process
a) the partial stream is fed to a distillation column containing at least 5 theoretical separation stages, and
b) in the distillation column, phenol is distilled off at the top, and
c) a first portion of the bottom product is discharged from the process, and
d) a second portion of the bottom product is transferred continuously into a dwell-time container in which the side products contained in the bottom product are at least partially isomerized at temperatures of >190° C. and with a hydrodynamic dwell time of at least 120 minutes, in the presence of an acidic catalyst, and then fed back into the distillation column, the flow rate of the portion of the bottom product fed into the dwell-time container being more than 30% of the flow rate of the partial stream introduced into the distillation column in step a).

The phenol distilled off in step b) preferably has a purity of >99.8 wt. %. The term "flow-rate" in the present context refers to the rate in Kg/hour of the flow of material. The technical object is achieved by acid-catalyzed cleavage of the discharged stream in a dwell-time container and continuous separation of the phenol over a vacuum column having a high separating capacity.

FIG. 1 shows a preferred embodiment of the process according to the invention.

A partial stream 1 discharged from a process for the preparation of bisphenol A is fed into a distillation column 2 having a high separating efficiency. The high separating efficiency is achieved by the theoretical separating stages, of which there are at least 5. In this distillation column, phenol vapours 3 are separated off at the top and are condensed in a condenser 4 to liquid phenol 5. The bottom product or discharge 6 from the column 2 is circulated via a heat exchanger (herein also called vaporizer) 7 so that the energy required for the vaporisation of phenol is thus introduced into the system. The condenser 4 and the vaporiser 7 may be independent parts of the installation or they may be integrated into the structure of the distillation columns. A partial stream 9 of the bottom product is fed to disposal in the form of residual resin, optionally after storage in a buffer tank 10.

Another partial stream 8 of the bottom product is fed to a dwell-time container 11. In this dwell-time container, the acid-catalyzed isomerization and cleavage of BPA and side products take place, with the formation of phenol. The cleavage is accelerated by the addition of suitable acids (stream 12) by means of a metering unit 13. The phenol-containing discharge 14 from the dwell-time container 11 is combined with the discharged partial stream 1 and thus fed back into the distillation unit 2 for the recovery of phenol.

The process is operated continuously and reaches an equilibrium state after a short time. The partial stream 1 discharged from the process for the preparation of bisphenol A may in principle be any product stream from a process for the preparation of BPA that contains the following components: from 40 to 90 wt. % phenol, from 5 to 40 wt. % bisphenol A and from 5 to 40 wt. % side products formed in the reaction of phenol and acetone to give bisphenol A.

Partial stream 1 is preferably a discharged partial stream from a BPA preparation process with suspension crystallization and solid/liquid separation, a partial stream of the filtrate of the solid/liquid separation for the discharge of side products being fed off in the direction of the process according to the invention for the separation of phenol. Before being fed into the distillation column 2, the mentioned partial stream 1 is optionally fed through an additional rearrangement unit, wherein a portion of the BPA contained in the filtrate is recovered by treatment with an acidic ion exchanger, subsequent partial distillation of phenol, crystallization and solid/liquid separation, and fed to the main process. In this case, the filtrate of the solid/liquid separation in the rearrangement unit is used as the feed stream 1 of the distillation column 2.

In order to permit cleavage, separation and purification of the phenol-containing residual substances in a manner that is as efficient as possible, the following conditions must be observed in the procedure according to the invention: the distillation column 2 must have at least 5 theoretical separation stages, preferably at least 10 theoretical separation stages, in order to permit the separation of other low-boiling components such as, for example, isopropenyl phenol and ensure concentration of the resulting phenol to a purity of >99.8 wt. % at the top of the column. The distillation is preferably carried out with an absolute pressure at the top of the column of from 70 to 200 mbar, preferably from 90 to 120 mbar. The dwell-time container 11 must be so constructed that a mean hydrodynamic dwell time of the circulating stream 8 of at least 2 hours, preferably at least 4 hours, is established, in order to achieve clearage of BPA and side products that is effective and as complete as possible. The dwell-time reactor may be operated completely filled with upward or downward flow or in a level-controlled manner.

The isomerization and the associated cleavage in the dwell-time container 11 in step d) is carried out in the presence of an acidic catalyst. As the acidic catalyst (stream 12) for the cleavage in step d) there may in principle be used a large number of strongly acidic, low or non-volatile Brönstedt acids, including phosphoric acid or the higher condensates thereof, sulfuric acid, alkanesulfonic acids having >4 carbon atoms in the alkane chain, aromatic sulfonic acids, arylalkane-sulfonic acids or phosphonium acids. In addition to these homogeneously employed acids, it is also possible to use heterogeneous cleavage catalysts, such as, for example, strongly acidic aluminium oxide, supported Lewis acids, acidic zeolites or other aluminas, or polystyrene sulfonic acids. In this case, the metering unit 13 is not required and the heterogeneous catalyst is introduced into the dwell-time container 11 by means of a suitable retaining construction and exchanged as necessary. In a preferred embodiment of the invention, the isomerization and cleavage in step d) are carried out in the presence of sulfuric acid, phosphoric acid or p-toluenesulfonic acid, particularly preferably with sulfuric acid. The metering may be carried out, as shown in FIG. 1, as a stream 12 via the metering unit 13 into the circulating stream of the bottom product of the distillation column 2. However, it is also possible for metering to be carried out into the intake stream 8 into the dwell-time container 11 or into the outlet stream 14 from the dwell-time container 11. Finally, metering may also be carried out into the partial stream 1 into the distillation column 2. Metering into the circulating stream of the bottom product of the distillation column 2 of the column is preferred.

The preferred concentration of the acidic cleavage catalyst is dependent on the amount of the cleavable side products in the intake stream and on the nature of the acid used and may readily be determined in simple experiments. For the preferred embodiment using sulfuric acid, the metered amount of acid is given as follows:

$$M(\text{sulfuric acid})=c^*(1-X)^*M(1)$$

where

M (sulfuric acid) represents the flow rate of sulfuric acid in kg/h, and c represents the concentration factor, and x represents the weight fraction of phenol in partial stream 1, and M(1) represents the flow rate of partial stream 1 in kg/h.

For effective cleavage, c is from 0.001% to 2%, preferably from 0.005 to 1%, particularly preferably from 0.01 to 0.2%. For other acids, analogous equations with 0.001%<c<5% apply.

For effective isomerization and cleavage, the temperature in the dwell-time container 11 must be >190° C., preferably >200° C. In order to limit the use of additional apparatuses, the supply of heat is effected in a preferred embodiment directly by the vaporiser 7 of the distillation column 2. This means that the intake stream 8 into the dwell-time container 11 is not heated by a separate heat exchanger and the bottom of the column 2 and the dwell-time container 11 are operated at the same temperature.

In order to ensure efficient separation of the phenol from the outlet stream 14 from the dwell-time container 11, it is necessary that the circulating stream via the dwell-time container should not be too small compared with the partial stream 1.

Otherwise, only incomplete cleavage of the cleavable side products occurs and material that is still cleavable is discharged via the discharged partial stream 9, which is associated with a loss of material. The flow rate introduced into the dwell-time container 11 is therefore >30%, preferably >80%, very particularly preferably >100% of the flow rate of the partial stream 1 coming from the process for the preparation of bisphenol A.

In order to allow the acid-catalyzed cleavage to proceed successfully, it is additionally necessary to select a hydrodynamic dwell time in the dwell-time container 11 of at least 2 hours, preferably at least 4 hours.

EXAMPLES

The following Examples 1 to 7 are carried out in a test installation according to FIG. 1.

An industrial installation for the preparation of bisphenol A yields, after reaction and separation of BPA, a discharged partial stream 1 which is fed to working up by distillation in the vacuum distillation column 2. The partial stream 1 is fed to the distillation column 2 with a flow rate M(1) and contains phenol in a weight fraction of X and other components in a weight fraction of (1−X), which other components substantially contain BPA and its isomers as well as various branched and higher condensation products of acetone and phenol, such as, for example, hydroxyphenyl-substituted indanes, chromanes, trisphenols and similar cleavable products. The composition (without the phenol component) in all the examples and comparison examples is: p,p-BPA 35-40 wt. %, o,p-BPA 9 to 12 wt. %, hydroxyphenyl-substituted indanes 15 to 19 wt. %, hydroxyphenyl-substituted chromanes 18 to 22 wt. %, trisphenol 3 to 5 wt. %, other constituents 9 to 12 wt. %.

This corresponds to a typical composition of a discharged stream from a bisphenol A production installation.

Table 1 shows the purity C(5) and the flow rate M(5) of the resulting phenol stream 5 at the top of the column for the various conditions on which Examples 1 to 7 are based. The column 2 used has 20 theoretical plates and was operated with a reflux ratio of about 0.6 and with the pressures that become established with establishment of the temperature T(11) at the bottom of the column 2 in thermodynamic equilibrium. The temperature in the dwell-time container 11 is the same as the temperature at the bottom of the column 2. The indicated values relate to equilibrium conditions, which become established after a few hours with continuous operation of the column.

For optimum recovery of phenol from the partial stream it is desirable to maximise the flow rate M(5) and the purity C(5) of the phenol stream 5 separated off, in order to obtain a maximum amount of highly pure phenol. At the same time, the flow rate M(9) of unusable residual resin 9 is to be minimize d. In Examples 1 and 2 according to the invention, the flow rate M(5) of the phenol stream 5 separated off is increased by the cleavage of the cleavable constituents contained in the partial stream 1, so that, based on the weight fraction X of phenol in the partial stream 1, a phenol yield $Y=M(5)/(X*M(1))$ of >1.20 is obtained and, at the same time, a phenol stream 5 of high purity C(5) is obtained and the flow rate M(9) of discharged residual resin 9 is minimized.

In Examples 1 to 3 and 5 to 7, cleavage in the dwell-time container 11 is assisted by the addition of sulfuric acid. The amounts of sulfuric acid M(sulfuric acid) used are given by the following equation: $M(\text{sulfuric acid})=c*(1-X)*M(1)$.

In Comparison Example 3, the temperature T(11) in the dwell-time container 11 is lowered to 180° C. The phenol yield falls to 1.03 as a result, i.e. effective cleavage no longer takes place.

Comparison Example 4 shows the effect of the sulfuric acid concentration. Without the feeding in of additional acid (c=0 in Example 4 means M(sulfuric acid)=0) there is no effective cleavage and the phenol yield therefore falls to 0.97.

Comparison Example 5 shows the effect of the flow rate of the stream of bottom product fed through the dwell-time container 11. Effective cleavage and recovery of phenol is only obtained with an adequate flow rate M(8) of the bottom product fed through the dwell-time container 11 and back into the column 2. For $M(8)<0.3*M(1)$, the phenol yield therefore falls to 1.05.

Comparison Example 6 is carried out with an otherwise identical construction using a column of lower separating efficiency (number of theoretical plates=1). Although a high phenol yield Y=1.27 is reached in this case, only moderate phenol purity (C(5)=96.2 wt. %) is achieved at the top of the column.

Comparison Example 7 is carried out with the column 2 already used in Examples 1 to 5, but the dwell-time container 11 is avoided so that no dwell time for cleavage is available. As a result, a high phenol yield Y in the phenol stream 5 is not achieved despite the addition of sulfuric acid.

The examples and comparison examples show that it is possible in the process according to the invention, using a distillation column 2 and a dwell-time container 11, with addition of an acidic cleavage catalyst, to obtain phenol of high purity in an increased yield at the top of the column and at the same time to minimize the amount of residual resin.

TABLE 1

|  | M(1) [t/h] | X [—] | c [%] | T(11) [° C.] | C(5) [wt. %] | M(5) [t/h] | Y [—] | M(9) [t/h] | M(8) [t/h] | τ(11) [h] |
|---|---|---|---|---|---|---|---|---|---|---|
| Ex. 1[1)2)] | 2.75 | 0.65 | 0.06 | 205 | 99.88 | 2.19 | 1.22 | 0.56 | 3.10 | 19.4 |
| Ex. 2[1)2)] | 2.40 | 0.50 | 0.06 | 210 | 99.91 | 1.72 | 1.43 | 0.68 | 2.95 | 20.3 |
| Comp. Ex. 3[1)2)] | 2.65 | 0.62 | 0.06 | 180 | 99.75 | 1.69 | 1.03 | 0.96 | 2.80 | 21.4 |
| Comp. Ex. 4[1)2)] | 2.80 | 0.59 | 0.0 | 205 | 99.87 | 1.60 | 0.97 | 1.20 | 3.05 | 19.7 |
| Comp. Ex. 5[1)2)] | 2.75 | 0.63 | 0.05 | 200 | 99.89 | 1.82 | 1.05 | 0.93 | 0.5 | 120.0 |
| Comp. Ex. 6[3)2)] | 2.90 | 0.62 | 0.06 | 205 | 96.25 | 2.28 | 1.27 | 0.62 | 3.2 | 18.8 |
| Comp. Ex. 7[1)4)] | 2.90 | 0.58 | 0.05 | 205 | 99.58 | 1.70 | 1.01 | 1.20 | 3.2 | 0 | where

M(1) = flow rate of partial stream 1,

X = weight fraction of phenol in partial stream 1,

C = concentration factor for sulfuric acid addition $M(H_2SO_4) = c * (1 - X) * M(1)$; 96% sulfuric acid was added, T(11) = temperature in the dwell-time container 11, C(5) = content of phenol in the phenol stream 5, M(5) = flow rate of the phenol stream 5, Y = phenol yield based on the content of phenol in partial stream 1: $Y = M(5)/(X * M(1))$, M(9) = flow rate of discharged residual resin 9 for disposal, M(8) = flow rate of bottom product through the dwell-time container 11, τ(11) = hydrodynamic dwell time in the dwell-time container 11.

Footnotes:

[1)]a vacuum column having 20 theoretical plates is used

[2)]a dwell-time container having a volume of 60 m³ is used

[3)]a vacuum column having 1 theoretical plate is used

[4)]the dwell-time container 11 is avoided

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A continuous process for the separation of phenol comprising
   (a) feeding a stream of material containing 40 to 90% phenol, 5 to 40% bisphenol A and 5 to 40% of side products into a distillation column containing at least 5 theoretical separation stages,
   b) distilling-off the phenol as a top product and discharging from said column a first portion of a bottom product containing side products,
   c) continuously introducing a second portion of the bottom product into a dwell-time container operating at process parameters sufficient to cause, in the presence of a sulfuric acid catalyst, an at least partial isomerization of the side products to form an isomerized product and
   d) introducing the isomerized product to the distillation column,
   wherein the introducing of said portion is at a rate, in Kg/hour, that is more than 30% of the rate of feeding, and where said process parameters include temperatures greater than 190° C. and hydrodynamic dwell time of at least 120 minutes, said stream produced in the course of preparing bisphenol A by reacting phenol with acetone.

2. The process according to claim 1, wherein the temperature is higher than 200° C.

3. The process according to claim 1 wherein the hydrodynamic dwell time is at least 4 hours.

4. The process according to claim 1 wherein the distilled-off phenol is characterized by having a purity greater than 99.8 wt. %.

* * * * *